US009668697B2

(12) United States Patent
Fandrey et al.

(10) Patent No.: US 9,668,697 B2
(45) Date of Patent: Jun. 6, 2017

(54) CATHETER AND CATHETER SYSTEM (71) Applicant: VascoMed GmbH, Binzen (DE)

(72) Inventors: Stephan Fandrey, Affoltern am Albis (CH); Ingo Weiss, Berlin (DE); Stefan Knorr, Berlin (DE)

(73) Assignee: VascoMed GmbH, Binzen (DE)

( * ) Notice: Subject to any disclaimer, the term of this patent is extended or adjusted under 35 U.S.C. 154(b) by 649 days.

(21) Appl. No.: 13/654,094

(22) Filed: Oct. 17, 2012

(65) Prior Publication Data

US 2013/0102868 A1 Apr. 25, 2013

Related U.S. Application Data (60) Provisional application No. 61/550,470, filed on Oct. 24, 2011.

(51) Int. Cl.
*A61B 5/04* (2006.01)
*A61B 5/00* (2006.01)
*A61B 90/00* (2016.01)
*A61B 8/14* (2006.01)
*A61M 31/00* (2006.01)
*A61B 18/18* (2006.01)
(Continued)

(52) U.S. Cl.
CPC ............ *A61B 5/6885* (2013.01); *A61B 90/06* (2016.02); *A61B 5/6852* (2013.01); *A61B 18/1492* (2013.01); *A61B 2090/065* (2016.02); *A61M 25/0082* (2013.01); *A61M 2025/0002* (2013.01); *A61N 1/05* (2013.01)

(58) Field of Classification Search
CPC ............ A61B 2090/064; A61B 5/6885; A61B 18/1492; A61B 2090/065; A61B 2562/0247; A61B 5/02154; A61B 5/065

USPC ................ 600/372–374, 381, 466, 508–509; 604/95.04; 606/20–52
See application file for complete search history.

(56) References Cited

U.S. PATENT DOCUMENTS 6,530,889 B1 * 3/2003 Konings et al. .............. 600/486
6,980,848 B2 * 12/2005 Helfer et al. ................. 600/423
(Continued)

FOREIGN PATENT DOCUMENTS

WO 9837434 8/1998
WO 2005011511 2/2005
(Continued)

*Primary Examiner* — Joseph Stoklosa
*Assistant Examiner* — Brian M Antiskay
(74) *Attorney, Agent, or Firm* — Buchanan Ingersoll & Rooney PC (57) ABSTRACT A catheter comprising an elongated and axially rigid catheter body which has a distal end and a proximal end in respect of an operating position, wherein a movable and/or deformable protection element or a corresponding protection section of the catheter body, which is provided with predetermined motion or deformation resistance, is disposed on the distal end, and transducer elements of a converter device for converting displacement into a non-mechanical quantity are provided in a stationary manner on the protection element or protection section, and corresponding pick-up elements of the converter device are provided on the catheter body, or vice versa, and wherein the catheter body comprises a lead for transmitting a measurement signal generated by the converter device to the proximal end, and a measuring connector on the proximal end.

10 Claims, 5 Drawing Sheets (51) Int. Cl.
  *A61M 25/00* (2006.01)
  *A61N 1/05* (2006.01)
  *A61B 18/14* (2006.01)

(56) References Cited

U.S. PATENT DOCUMENTS

| | | | |
|---|---|---|---|
| 7,848,789 B2 * | 12/2010 | Govari | A61B 5/0538 600/424 |
| 2008/0009750 A1 | 1/2008 | Aeby et al. | |
| 2008/0051704 A1 | 2/2008 | Patel et al. | |
| 2008/0275428 A1 | 11/2008 | Tegg et al. | |
| 2009/0138007 A1 | 5/2009 | Govari et al. | |
| 2009/0177095 A1 | 7/2009 | Aeby et al. | |

FOREIGN PATENT DOCUMENTS

| | | |
|---|---|---|
| WO | 2008003307 | 1/2008 |
| WO | 2009007857 | 1/2009 |
| WO | 2011022665 | 2/2011 |

* cited by examiner

CATHETER AND CATHETER SYSTEM

CROSS-REFERENCE TO RELATED APPLICATIONS

This patent application claims the benefit of U.S. Provisional Patent Application No. 61/550,470, filed on Oct. 24, 2011, which is hereby incorporated by reference in its entirety.

TECHNICAL FIELD

The present invention generally relates to a catheter comprising an elongated catheter body which has a distal end and a proximal end in respect of an operating position. It furthermore relates to a catheter system comprising such a catheter and a measuring device attached thereto.

BACKGROUND

In the field of medicine, a large number of catheters having various designs or catheter-like devices (e.g., electrode leads) are known and are used on a large scale. They are used in part by experienced specialists, but also in part by physicians or medical personnel who do not have special knowledge or experience. Regardless of whether the user is experienced or not, harm or injury to the patient must be reliably ruled out.

When known catheters comprising a plastic or metal tip are used, there is risk of perforation. To minimize the surface pressure and, therefore, the risk of perforation, compromises must be struck in respect of the stiffness of the catheter shaft and the catheter tip. Under certain circumstances, these compromises limit the maneuverability and positional stability of the catheter. In addition, conventional catheters or electrode leads are "blind" when wall contact occurs in a vessel or hollow organ, i.e., they are incapable of providing the operator with information related to the contact. To assess the situation, the operator must rely on his/her manual dexterity and x-ray monitoring, if available.

Developments in recent years have focused on implementing a contact or force sensor function on a distal catheter tip. For example, International Publication No. WO 2005/011511 makes known a related force sensor based on optical fibers, in the case of which light transmitted to the catheter tip via a first optical fiber and directed back from the tip via a second optical fiber is modulated via reflectance in a deformation region on the catheter tip and, therefore, contact is detected. Additionally, International Publication No. WO 2008/003307 makes known an electrically operating force sensor for detecting a force vector, which can likewise be used on a catheter or a similar technical medical device.

Another group of developers is responsible for a series of publications which describe a three-axial fiber optic force sensor and a catheter equipped therewith: see, for example U.S. Publication No. 2008/0009750, International Publication No. WO 2009/007857 and/or U.S. Publication No. 2009/0177095. The optical fiber force sensor system used in this context operates according to the Fabry-Perot principle with a cylinder segmented in the longitudinal direction in the distal end region of the catheter body, and utilizes changes in reflectivity at the gaps between the cylinder segments to detect contact at the catheter tip.

A problem addressed by the present invention is that of providing an improved catheter which can be used even by less experienced personnel without risk of harm or injury to the patient, yet is designed such that the requirements for clinical application are still met and the use-value thereof is increased overall.

The present invention is directed toward overcoming one or more of the above-identified problems.

SUMMARY

A problem is solved by a catheter having the features of the independent claim(s). A catheter system having the features of the improved catheter of the independent claim(s) is also provided.

The subject matter of the application is based on the idea of modifying known catheter designs by providing a special movable and/or deformable protection element (or a protection section of the catheter body designed accordingly) on the distal end of the catheter. According to a further premise of the inventor(s), this protection element, or this protection section, is provided with predetermined motion or deformation resistance. Furthermore, the subject matter of this application is based on the idea of obtaining data from the motion or deformation of the protection element, or protection section, via suitable measurement equipment, said data enabling the specific situation to be better evaluated. To this end, a transducer/pick-up configuration must be positioned relative to the axially rigid catheter body and relative to the movable or deformable protection element, or protection section, in a distributed manner such that it sufficiently detects relevant motions or deformations.

In an embodiment of the subject matter of the application, the predetermined motion or deformation resistance is attained via a spring force of an elastic attachment of the protection element or a natural elasticity of the protection section. A special retention or suspension element having suitably selected spring or elasticity constants can therefore be provided, or a deformable protection element or a deformable protection section of the distal catheter end can be provided, with the desired natural elasticity by selecting a suitable material and dimensions.

In further preferred embodiments, at least three transducer or pick-up elements are distributed about a longitudinal axis or a virtually extended longitudinal axis of the catheter body, in particular, being distributed evenly, in order to record a displacement of the protection element or the protection section using vectors. In a first embodiment of this principle, exactly three pick-up elements which are distributed evenly, in particular, about the longitudinal axis with an angular separation of 120°, or pick-up systems which receive spatially resolved signals are assigned to exactly one transducer element. According to another embodiment, exactly three pick-up elements which are distributed evenly, in particular, about the longitudinal axis with an angular separation of 120°, are assigned to one pick-up system which receives spatially resolved signals.

In further embodiments, the transducer element comprises a light-emitting element, and the pick-up element, in particular, every pick-up element in a pick-up system, comprises a photodetector element. The pick-up system can comprise a charge-coupled device ("CCD") row or CCD matrix in particular. In further embodiments, a flat color filter or a polarization filter having locally varying filter characteristics is assigned to the—or at least one—light-emitting element, or to the—or at least one—photodetector. Further embodiments of the optical detection principle, which are described below, are also possible.

In another fundamental embodiment, the transducer element and the pick-up element each comprise at least one electrode or an electrical contact for applying a measuring voltage and for detecting a measuring current, or vice versa. In useful embodiments, such a catheter comprises at least one linear or flat electrode or resistor array, and one substantially punctiform scanning contact or capacitive tap as the transducer and pick-up elements, wherein one of the electrode or resistor arrays, or the scanning contact, is attached in a stationary manner to the rigid catheter body, and the other is attached in a stationary manner to the protection element or protection section. Further embodiments are also possible within the scope of this measurement principle, and are discussed below.

In further implementations, timing means are assigned to the transducer or pick-up elements to enable predetermined temporal control of their activation or location on a predetermined trajectory in the region of the protection element or protection section, and the pick-up elements are designed to receive signals time resolved.

In one embodiment having great practical significance, the catheter is designed as an electrode lead comprising at least one stimulation and/or sensing electrode. The catheters of the subject matter of the application can also be designed as ablation catheters for connection to a high-frequency device, or as purely mechanically operating catheters, such as, for example, dilatation or stent insertion catheters.

A catheter system of the subject matter of the application comprises, in addition to a catheter covered by this application, a measuring unit connected to the measuring connector for determining a displacement of the protection element or protection section and/or a pressure acting thereon. Useful embodiments of the measuring unit mentioned herein will become apparent largely from the above-mentioned different embodiments of the transducer/pick-up elements used. In a special embodiment, the above-mentioned timing means for a predetermined temporal control of the activation or the location of the transducer or pick-up elements is designed as a component of the measuring unit connected to the catheter.

The following are aspects of further embodiments of the subject matter of this application: the transducer elements are also referred to as a "source", the pick-up elements as a "sensor", the converter device as a "recoding unit", and the protection section of the catheter is also referred to as a "jacket".

- The deformation body is comprised of two parts that are displaceable relative to one another (e.g., an inner cylinder relative to the jacket of a catheter).
- There is at least one recoding unit, preferably three which are distributed 120° apart around the cylinder circumference.
- The three recoding units use the same sensor (e.g., in the inner cylinder) and three sources in the jacket.
- The recoding of the (three) longitudinal deformation(s) (e.g., due to the compression or bending of the catheter) into location information takes place on a sensor with resolution (e.g., CCD row, CCD chip, photodiode (array), etc.).
- The primary location information (deformation) is converted via a filter into frequency information (e.g., source=light, filter=color wedge, sensor=color sensor).
- The recoding unit can also convert the nature of the signal for transmission purposes (e.g., light into color per location (RGB); via local sensor; an electrical signal is transmitted de facto, etc.).
- The location information is recoded into phase information.
- The location information is recoded into polarization information (e.g., polarization filter that can change position).
- The location information is recoded into time information (e.g., multiplex procedure, scanning procedure; z.B. the light source strikes the position of the sensors).
- The recoding takes place via sliding contact; the sensor is a linear potentiometer.
- Scanning takes place via active linear motion of the source or the sensor.
- Scanning takes place via rotation (e.g., helical light slit on the inner cylinder).
- Scanning takes place via sliding contact and strikes a sense contact.
- A coupling of coils is used to detect the deformation.
- A capacitive coupling is used to detect the deformation.
- An acoustic coupling is used to detect the deformation.
- A resonant coupling is used to detect the deformation.
- The linear position is tracked on a code pattern using a scratching needle (e.g., similar to the AFM principle).

The catheter according to the subject matter of the application makes it possible, in one or more embodiments, to characterize an existing wall contact of the catheter with the wall of a vessel or a hollow organ using measurement technology. It is therefore possible to measure the force with which the catheter presses onto the bodily tissue in a certain insertion situation. In conjunction therewith, improvements can be made to sensing and stimulation processes, or even ablation procedures, and, in particular, risks of perforation can be largely minimized.

Advantages, aspects, objects, applications and useful features of the subject matter of the application will also become apparent from a study of the basic description that follows of embodiments and examples described below, in combination with the Figures, and the appended claims.

DESCRIPTION OF THE DRAWINGS

The inventive subject matter will be described in greater detail in the following using preferred exemplary embodiments, with reference to the drawings and the reference characters noted therein. The Figures show.

DETAILED DESCRIPTION

Figure 1A:
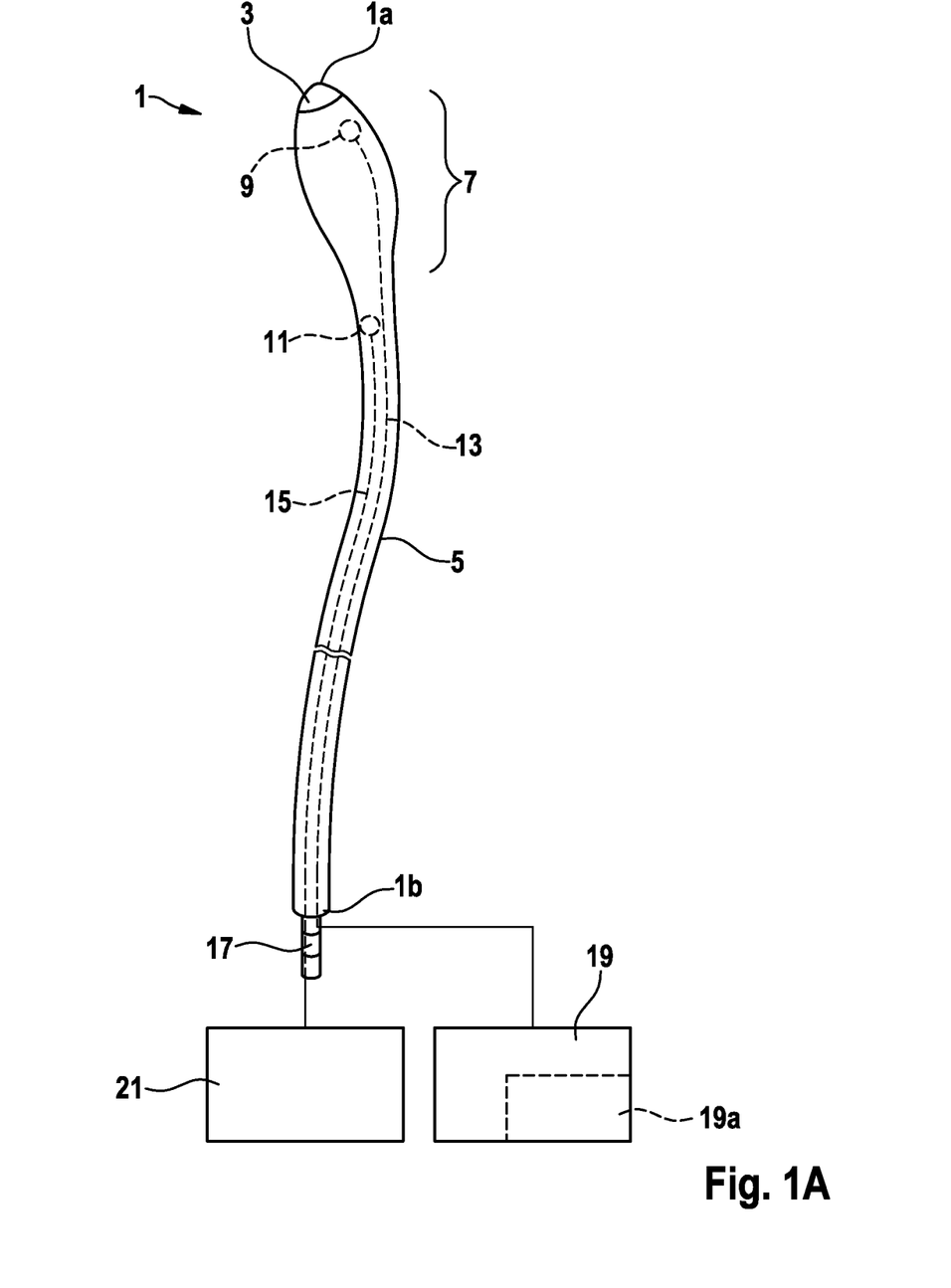
FIGS. 1A-1B each shows a schematic diagram of an embodiment of the catheter according to the subject matter of the application.

FIG. 1A shows a schematic depiction of an electrode lead 1 of a catheter according to the subject matter of the application, which comprises a distal end 1a and a proximal end 1b, and a tip electrode 3 on the distal end. Electrode lead 1 further comprises a catheter body 5, which is stiff but flexible in the axial direction, the distal region 7 of which is designed as a deformable protection section made of an elastically deformable material.

A transducer element 9 of a converter device is placed near the distal end of the protection section 7, and an adapted pick-up element 11 of the converter device is positioned on the proximal end of the protection section 7 and, therefore, in the distal end region of the rigid section of catheter body 5. Transducer element 9 is connected via a control lead 13, and pick-up element 11 is connected via a measuring lead 15—both of which extend longitudinally through the catheter body 5—to a connecting plug 17 on the proximal end 1b. Control lead 13 is connected to a measurement control unit 19, and measuring lead 15 is connected to a measuring unit 21, via appropriate annular contacts on connecting plug 17. In the embodiment shown, measurement control unit 19 includes a timer 19a for running a measurement program that has a predetermined run time.

In the catheter system depicted in FIG. 1A, a deformation (compression and/or bending) of protection section 7, which is caused by wall contact with a certain level of force, is "recoded" into a measurement signal of pick-up element 11. The measurement signal is transmitted, via measuring lead 15, to measuring unit 21, which performs an appropriate evaluation and obtains an evaluation result that characterizes the wall contact of electrode lead 1, which an operator can take into account in his/her next steps, such as, for example, determining the optimal placement and pressure of tip electrode 3.

Figure 1B:
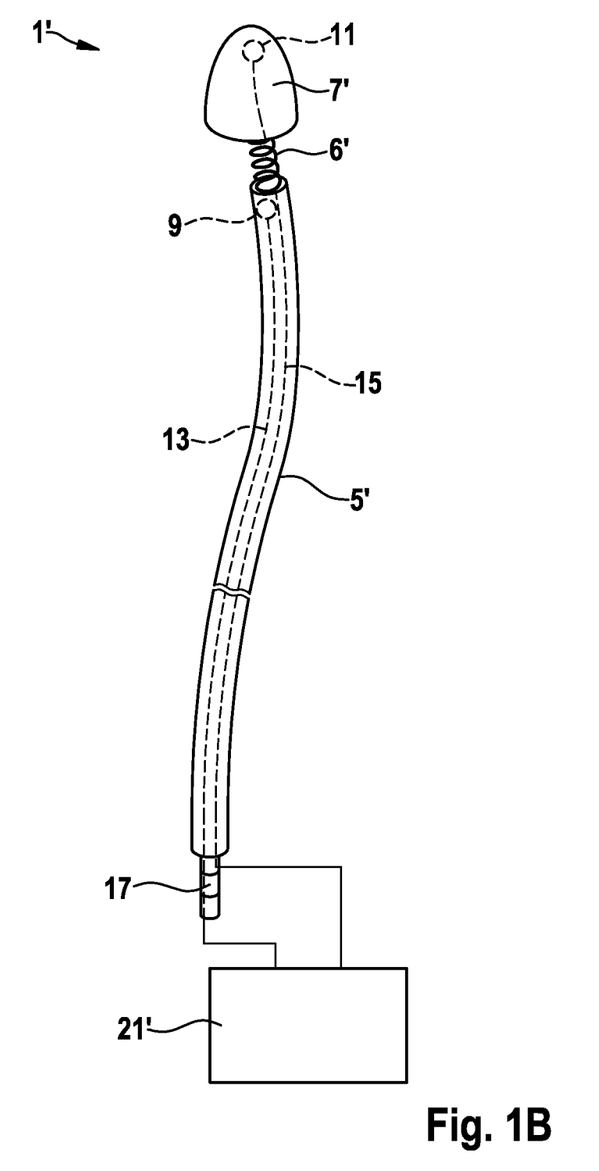

FIG. 1B shows, as an embodiment that has been modified relative to the embodiment depicted in FIG. 1A. In FIG. 1B, parts of the catheter 1' that are identical or that perform the same function as those in FIG. 1A are labeled therein with the same reference numerals. The main difference is that an axially stiff catheter body 5' is provided in the exemplary embodiment of FIG. 1B without an integrated protection section. The integrated protection section is replaced by a protection element 7' that is held distally via an elastic suspension 6' on catheter body 5'.

For the rest, transducer element 9 and pick-up element 11 are reversed in regard to their positioning compared to the system according to FIG. 1A and, instead of separate measurement control units and measuring units, the system comprises an integrated control and measuring unit 21'. The function of the system is substantially as described above, and the integrated control and measuring unit 21' is suited especially for an electrical or electromagnetic embodiment of the converter device, which is comprised of transducer element 9 and pick-up element 11, in which the current intensity resulting from an applied measuring voltage is approximately measured.

Figure 2:
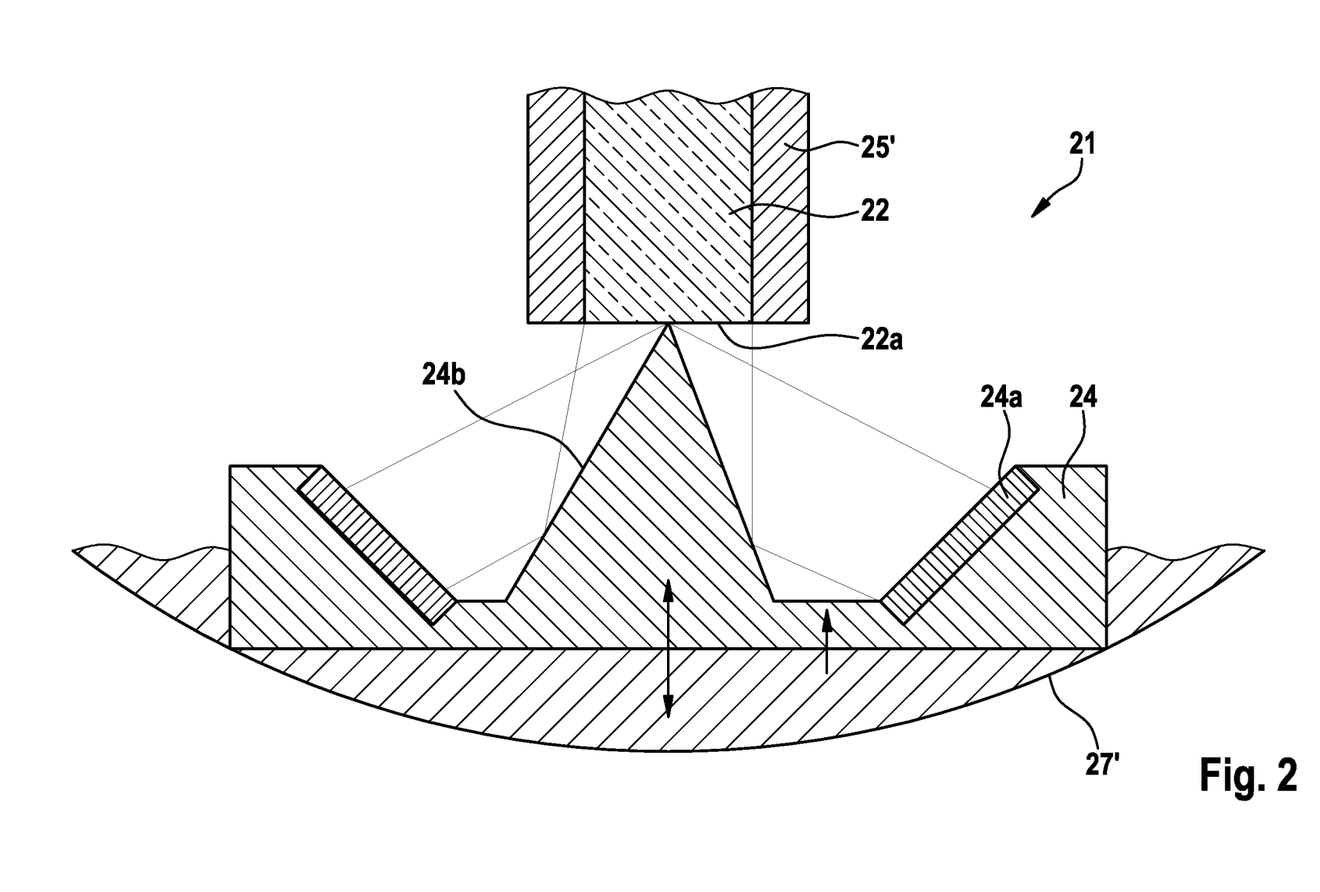
FIG. 2 shows a schematic diagram of a further embodiment.

FIG. 2 shows, as a sectional view of the distal end of a catheter 21, an optical measuring technique implemented therein. The reference characters are based in part on the depiction in FIG. 1B. An optical fiber device 22, the outlet opening 22a of which on the distal end of the stiff catheter body functions as an optical transducer element, is installed in a substantially stiff catheter body 25'. A protection element 27' (which is shown herein enlarged and not-to-scale and only as a section) is installed on the end of catheter body 25' using a suspension (not depicted) having a predetermined elasticity.

A specially shaped measurement pick-up base body 24 is situated in protection element 27', in which three photodiode arrays 24a, distributed about the extended longitudinal axis of the catheter body 25' at regular angular intervals, are integrated, as pick-up systems, at a slant relative to the catheter longitudinal axis. A three-sided pyramid 24b is situated centrally in measuring pick-up body 24, via which the measurement light exiting the light exit surface 22a is cast onto pick-up systems 24a. Via appropriate measuring leads (not depicted), a measurement signal is tapped at each of the photodiode arrays 24a, and is transmitted to the measuring unit of the catheter system. If the catheter tip makes wall contact, protection element 27' is displaced and/or rotates, thereby changing a differential signal between the photodiode arrays 24a depending on the direction and extent of the deformation, thereby enabling the displacement and/or rotation to be determined via a suitable evaluation of the measurement signals.

Figure 3:
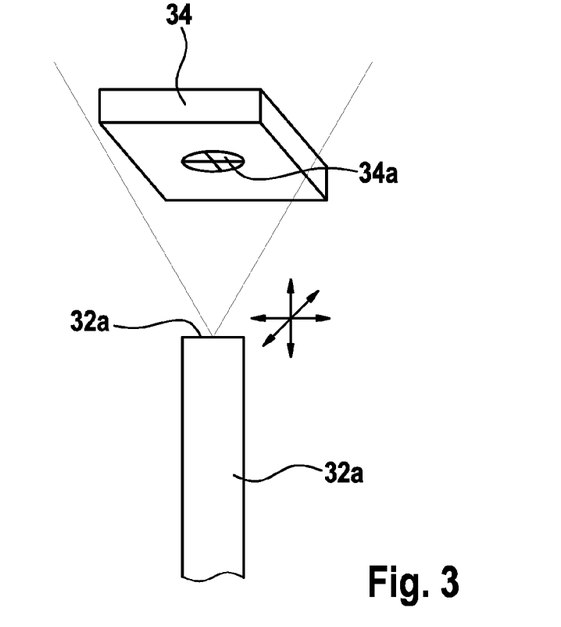
FIG. 3 shows a schematic diagram of a further embodiment.

FIG. 3 shows a sketch of a further optoelectrical converter device comprising an optical fiber 32, which serves as a transducer element, comprising an exit pupil 32a and a pick-up element 34, which comprises a four-quadrant measuring device 34a comprised of four photodiodes. When pick-up element 34 rotates or is displaced laterally relative to the axis of the optical fiber 32 and, therefore, the center of light exit position 32a, the individual photodiodes are illuminated with different intensities, thereby making it possible to deduce the extent of the displacement or rotation via the evaluation of a differential signal. This system makes it possible, to a certain extent, to perform a vector-based evaluation.

Figure 4:
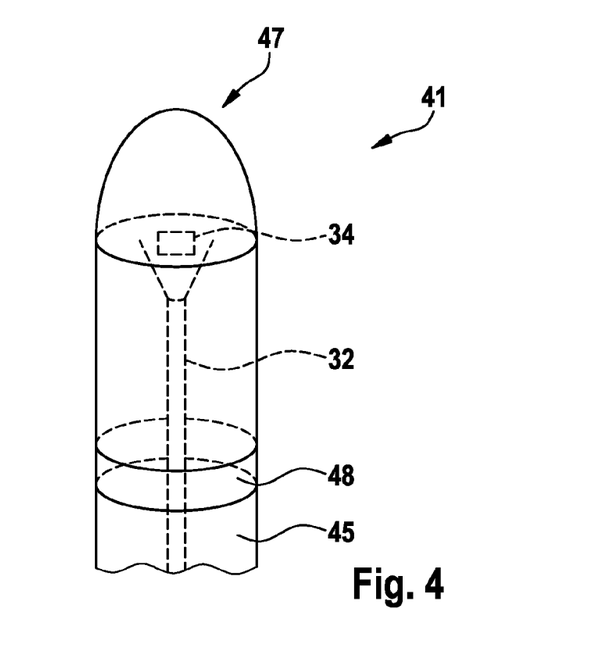
FIG. 4 shows a schematic diagram of a further embodiment.

FIG. 4 shows how the elements of FIG. 3 can be incorporated into the distal end section of a catheter 41. Akin to FIG. 1A, the catheter body is labeled here with numeral 45, and the distal protection section thereof is labeled with numeral 47. A ring electrode 48 is also shown, as an example, which can be provided in an embodiment of catheter 41 as an electrode lead. As shown herein, if deformation occurs in the axial direction of the catheter and optical fiber 32, the light intensity that is received will also change, and therefore compressions of the catheter device caused by wall contact can also be detected via the lateral displacements and rotations mentioned above.

Figure 5:
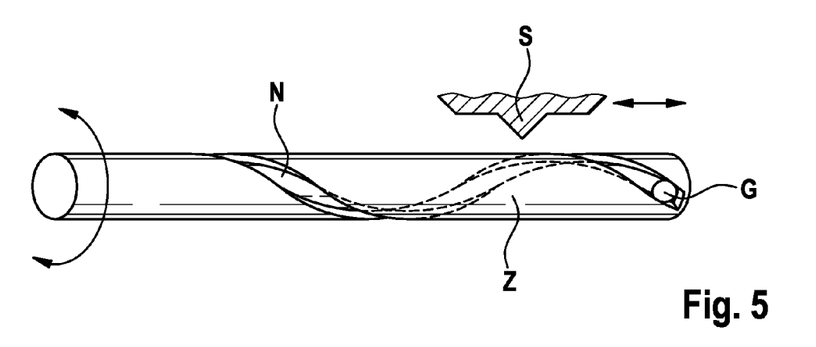
FIG. 5 shows a schematic diagram of a further embodiment.

FIG. 5 shows a sketch to illustrate another measurement principle which can be used in the inventive catheter. A transducer element G, which is guided in a cylinder Z having a groove N that extends in a spiral over the wall, is assigned to a stationary pick-up element S. If the sensor is connected to the movable or deformable protection element or protection section, provided rotation of the fiber is timed precisely, a light beam exiting transducer element G strikes pick-up element S at an earlier or later instant depending on the specific position thereof, and so the instant at which a signal is detected indicates the amount of a displacement to which the fastening point of the pick-up element is subjected. Deformation of the catheter tip caused by wall contact can therefore be deduced on the basis of the time in point at which a signal was detected.

A further embodiment that functions on an optical basis can be attained via a punctiform light source in the center of the catheter tip which is movably supported relative to, for example, a CCD row or a photodiode array. If force is applied from the outside, relative motion occurs between the light source and the CCD row, and so the application of force can be deduced from this signal. To measure a 3D force, three CCD rows are disposed about the light source at angular intervals of 120°. A force vector can therefore be determined on the basis of the location information of the light source relative to the individual CCD rows. Alternatively, for example, three light sources can also be disposed around a CCD row, thereby making it possible to calculate a 3D force vector on the basis of the displacements of the three light sources.

In a further embodiment, the deformation is recoded into a spectral displacement. This can take place by way of a longitudinally disposed light source, for example, which changes its spectrum from the distal end to the proximal end. If this light source moves along a window, behind which a detector is located, the deformation can also be deduced on the basis of the wavelength that is detected. A further embodiment functions in a similar manner, except that the phase changes in this case.

In a further embodiment, a polarization filter is accommodated between the light source and the detector. The polarization filter changes its polarization direction along the catheter, and so the polarization of the light received by a photodetector installed on the movable catheter end changes when the catheter tip is deformed. To measure the polarization, the signal can be transmitted back to an evaluation unit via a polarization-maintaining fiber.

Figure 6:
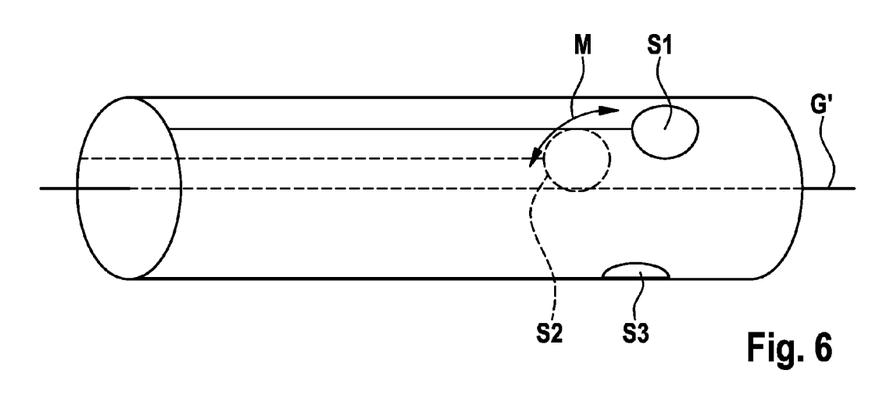
FIG. 6 shows a schematic diagram of a further embodiment.

FIG. 6 shows a sketch of a further measurement principle, in which pick-up elements S1, S2, S3 (distributed around the circumference at regular angular intervals) in the form of coils are situated opposite an electric transducer element G' (approximately a wire through which current flows) guided centrally in the catheter body on a jacket section of a deformable catheter end 3. If the current induced in the three pick-up coils is the same in an underformed catheter without wall contact, the currents that are detected when a catheter is deformed are different, and the evaluation thereof yields statements about the deformation state caused by wall contact.

In other embodiments which function electrically, an approximately punctiform pick-up element on the stiff catheter body, for example, can have sliding contact with a flat resistor region which is fixedly installed on the protection element or protection section and moves relative to the punctiform transducer element when deformation occurs. When a predetermined voltage is applied between the resistance region, acting as transducer element, and the pick-up element, a measuring current that is dependent upon the relative position between the two is detected, and can be used to determine the actual deformation of the catheter end. A capacitive tap can also be attained in a similar manner, in a further embodiment.

The embodiment of the subject matter of the application is not limited to the above-described examples and emphasized aspects but, rather, is possible in a large number of modifications that lie within the scope of handling by a person skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A catheter comprising:
    an elongated and axially rigid catheter body which has a distal end and a proximal end in respect of an operating position, wherein a deformable protection section of the catheter body, which is provided with predetermined deformation resistance, is disposed on the distal end, and a transducer element of a converter device for converting displacement into a non-mechanical quantity is provided on a distal end of the protection section, and a corresponding pick-up element of the converter device is provided in a stationary manner on a proximal end of the protection section, wherein the catheter body comprises a lead for transmitting a measurement signal generated by the converter device to the proximal end, and a measuring connector on the proximal end, wherein the transducer element comprises a light-emitting element, and the pick-up element comprises a photodetector element, wherein a flat color filter or a polarization filter is assigned to the light-emitting element, or to the photodetector element so that location information from the non-mechanical quantity is converted into frequency information or polarization information to deduce an extent to which displacement of the protection section occurs,
    wherein the light-emitting element comprises an elongated fiber-optic element guided in a spiral groove formed in an outer wall of a cylinder provided in the protection section of the catheter body, and
    wherein displacement of the protection section is deduced based on a point in time a light beam signal exiting the fiber-optic element is detected by the stationary photodetector element.

2. The catheter according to claim 1, wherein the predetermined deformation resistance is attained via natural elasticity of the protection section.

3. The catheter according to claim 1, wherein at least three pick-up elements are evenly distributed about a longitudinal axis or a virtually extended longitudinal axis of the catheter body.

4. The catheter according to claim 3, wherein exactly three pick-up elements are evenly distributed about the longitudinal axis with an angular separation of 120° and are assigned to exactly one transducer element.

5. The catheter according to claim 4, wherein the exactly three pick-up elements are assigned to one pick-up system which picks up spatially resolved signals.

6. The catheter according to claim 5, wherein the pick-up system comprises a charge-coupled device (CCD) row or CCD matrix.

7. The catheter according to claim 1, wherein the flat color filter or the polarization filter has locally varying filter characteristics.

8. The catheter according to claim 1, further comprising timing means assigned to the transducer or pick-up element to enable predetermined temporal control of their activation or location on a predetermined trajectory in the region of the protection section, and wherein the pick-up element is designed to pick up time resolved signals.

9. The catheter according to claim 1, wherein the catheter is in the form of an electrode lead having at least one stimulation and/or sensing electrode.

10. A catheter system comprising:
    a catheter according to claim 1, and
    a measuring unit connected to the measuring connector for determining a displacement of the protection section and/or a pressure acting thereon.

* * * * *